United States Patent
Alstad et al.

(10) Patent No.: US 10,474,792 B2
(45) Date of Patent: Nov. 12, 2019

(54) DYNAMIC TOPOLOGICAL SYSTEM AND METHOD FOR EFFICIENT CLAIMS PROCESSING

(71) Applicant: Change Healthcare Holdings, LLC, Nashville, TN (US)

(72) Inventors: Colin Erik Alstad, San Mateo, CA (US); Theodore Tanner, San Mateo, CA (US); Denise Koessler Gosnell, San Mateo, CA (US)

(73) Assignee: Change Healthcare Holdings, LLC, Nashville, TN (US)

( * ) Notice: Subject to any disclaimer, the term of this patent is extended or adjusted under 35 U.S.C. 154(b) by 0 days.

(21) Appl. No.: 14/939,973

(22) Filed: Nov. 12, 2015

(65) Prior Publication Data

US 2016/0342751 A1 Nov. 24, 2016

Related U.S. Application Data

(63) Continuation of application No. 14/715,380, filed on May 18, 2015, now abandoned.

(51) Int. Cl.
| | |
|---|---|
| *G16H 50/70* | (2018.01) |
| *G06F 19/00* | (2018.01) |
| *G06Q 40/08* | (2012.01) |
| *G06Q 50/22* | (2018.01) |
| *G06Q 10/10* | (2012.01) |

(52) U.S. Cl.
CPC .......... *G06F 19/328* (2013.01); *G06Q 10/10* (2013.01); *G06Q 40/08* (2013.01); *G06Q 50/22* (2013.01)

(58) Field of Classification Search
CPC ...................................................... G16H 50/70
USPC ......................................................... 705/2, 4
See application file for complete search history.

(56) References Cited

U.S. PATENT DOCUMENTS

| | | |
|---|---|---|
| 5,872,021 A | 2/1999 | Matsumoto et al. |
| 6,546,428 B2 | 4/2003 | Baber et al. |
| 7,386,565 B1 | 6/2008 | Singh et al. |
| 7,917,378 B2 | 3/2011 | Fitzgerald et al. |
| 7,917,515 B1 | 3/2011 | Lemoine |
| 7,970,802 B2 | 6/2011 | Ishizaki |
| 7,992,153 B2 | 8/2011 | Ban |
| 8,073,801 B1 | 12/2011 | Von Halle et al. |
| 8,095,975 B2 | 1/2012 | Boss et al. |
| 8,103,667 B2 | 1/2012 | Azar et al. |

(Continued)

FOREIGN PATENT DOCUMENTS

| | | |
|---|---|---|
| GB | 2478440 | 10/2013 |
| WO | WO 2012/122065 | 9/2012 |

OTHER PUBLICATIONS

"A simplicial complex, a hypergraph, structure in the altent semantic space of document clustering"; Lin et al.; Elsevier, 2005.*

(Continued)

*Primary Examiner* — John A Pauls
(74) *Attorney, Agent, or Firm* — Meunier Carlin & Curfman LLC

(57) ABSTRACT

A dynamic topological system and method for efficient claims processing are provided. The dynamic topological system and method for efficient claims processing may be used in a healthcare system. The dynamic topological system and method for efficient claims processing is easily extensible, maintainable and extendable.

18 Claims, 14 Drawing Sheets

(56) References Cited

U.S. PATENT DOCUMENTS

| | | | |
|---|---|---|---|
| 8,103,952 B2 | 1/2012 | Hopp | |
| 8,203,562 B1 | 6/2012 | Alben et al. | |
| 8,229,808 B1 | 7/2012 | Heit | |
| 8,286,191 B2 | 10/2012 | Amini et al. | |
| 8,359,298 B2 | 1/2013 | Schacher et al. | |
| 8,364,501 B2 | 1/2013 | Rana et al. | |
| 8,417,755 B1 | 4/2013 | Zimmer | |
| 8,495,108 B2 | 7/2013 | Nagpal et al. | |
| 8,515,777 B1 | 8/2013 | Rajasenan | |
| 8,527,522 B2 | 9/2013 | Baron | |
| 8,817,665 B2 | 8/2014 | Thubert et al. | |
| 8,984,464 B1 | 3/2015 | Mihal et al. | |
| 9,165,045 B2 | 10/2015 | Mok et al. | |
| 9,208,284 B1 | 12/2015 | Douglass | |
| 2002/0022973 A1 | 2/2002 | Sun et al. | |
| 2002/0038233 A1 | 3/2002 | Shubov et al. | |
| 2002/0165738 A1 | 11/2002 | Dang | |
| 2003/0055668 A1 | 3/2003 | Saran et al. | |
| 2003/0097359 A1 | 5/2003 | Ruediger | |
| 2003/0171953 A1 | 9/2003 | Narayanan et al. | |
| 2003/0217159 A1 | 11/2003 | Schramm-Apple et al. | |
| 2003/0233252 A1 | 12/2003 | Haskell et al. | |
| 2004/0143446 A1 | 7/2004 | Lawrence | |
| 2005/0010452 A1 | 1/2005 | Lusen | |
| 2005/0071189 A1 | 3/2005 | Blake et al. | |
| 2005/0102170 A1 | 5/2005 | Lefever et al. | |
| 2005/0137912 A1* | 6/2005 | Rao | G06Q 10/10 705/4 |
| 2005/0152520 A1 | 7/2005 | Logue | |
| 2005/0182780 A1 | 8/2005 | Forman et al. | |
| 2005/0222912 A1 | 10/2005 | Chambers | |
| 2006/0036478 A1 | 2/2006 | Aleynikov et al. | |
| 2006/0074290 A1 | 4/2006 | Chen et al. | |
| 2006/0089862 A1 | 4/2006 | Anandarao et al. | |
| 2006/0129428 A1 | 6/2006 | Wennberg | |
| 2006/0136264 A1 | 6/2006 | Eaton et al. | |
| 2007/0113172 A1 | 5/2007 | Behrens et al. | |
| 2007/0118399 A1 | 5/2007 | Avinash et al. | |
| 2007/0156455 A1 | 7/2007 | Tarino et al. | |
| 2007/0174101 A1 | 7/2007 | Li et al. | |
| 2007/0180451 A1 | 8/2007 | Ryan et al. | |
| 2007/0214133 A1 | 9/2007 | Liberty et al. | |
| 2007/0233603 A1 | 10/2007 | Schmidgall et al. | |
| 2007/0260492 A1 | 11/2007 | Feied et al. | |
| 2007/0276858 A1 | 11/2007 | Cushman et al. | |
| 2007/0288262 A1 | 12/2007 | Sakaue et al. | |
| 2008/0013808 A1 | 1/2008 | Russo et al. | |
| 2008/0046292 A1 | 2/2008 | Myers | |
| 2008/0082980 A1 | 4/2008 | Nessland et al. | |
| 2008/0091592 A1 | 4/2008 | Blackburn et al. | |
| 2008/0126264 A1 | 5/2008 | Tellefsen et al. | |
| 2008/0133436 A1 | 6/2008 | Di Profio | |
| 2008/0288292 A1 | 11/2008 | Bi et al. | |
| 2008/0295094 A1 | 11/2008 | Korupolu et al. | |
| 2008/0319983 A1 | 12/2008 | Meadows | |
| 2009/0083664 A1 | 3/2009 | Bay | |
| 2009/0125796 A1 | 5/2009 | Day et al. | |
| 2009/0192864 A1 | 7/2009 | Song et al. | |
| 2009/0198520 A1 | 8/2009 | Piovanetti-Perez | |
| 2009/0300054 A1 | 12/2009 | Fisher et al. | |
| 2009/0307104 A1 | 12/2009 | Weng | |
| 2009/0313045 A1 | 12/2009 | Boyce | |
| 2010/0076950 A1 | 3/2010 | Kenedy et al. | |
| 2010/0082620 A1 | 4/2010 | Jennings, III et al. | |
| 2010/0088108 A1 | 4/2010 | Machado | |
| 2010/0088119 A1 | 4/2010 | Tipirneni | |
| 2010/0138243 A1 | 6/2010 | Carroll | |
| 2010/0217973 A1 | 8/2010 | Kress et al. | |
| 2010/0228721 A1 | 9/2010 | Mok et al. | |
| 2010/0295674 A1 | 11/2010 | Hsieh et al. | |
| 2010/0332273 A1 | 12/2010 | Balasubramanian et al. | |
| 2011/0015947 A1 | 1/2011 | Erry et al. | |
| 2011/0055252 A1 | 3/2011 | Kapochunas et al. | |
| 2011/0071857 A1 | 3/2011 | Malov et al. | |
| 2011/0137672 A1 | 6/2011 | Adams et al. | |
| 2011/0218827 A1 | 9/2011 | Kennefick et al. | |
| 2011/0270625 A1 | 11/2011 | Pederson et al. | |
| 2012/0035984 A1 | 2/2012 | Srinivasa et al. | |
| 2012/0078940 A1 | 3/2012 | Kolluri et al. | |
| 2012/0130736 A1 | 5/2012 | Dunston et al. | |
| 2012/0158429 A1 | 6/2012 | Murawski et al. | |
| 2012/0158750 A1 | 6/2012 | Faulkner et al. | |
| 2012/0173279 A1 | 7/2012 | Nessa et al. | |
| 2012/0245958 A1 | 9/2012 | Lawrence et al. | |
| 2012/0246727 A1 | 9/2012 | Elovici et al. | |
| 2012/0290320 A1 | 11/2012 | Kurgan et al. | |
| 2012/0290564 A1 | 11/2012 | Mok et al. | |
| 2013/0030827 A1 | 1/2013 | Snyder et al. | |
| 2013/0044749 A1 | 2/2013 | Eisner et al. | |
| 2013/0085769 A1 | 4/2013 | Jost et al. | |
| 2013/0138554 A1 | 5/2013 | Nikankin et al. | |
| 2013/0166552 A1 | 6/2013 | Rozenwald et al. | |
| 2013/0204940 A1 | 8/2013 | Kinsel et al. | |
| 2013/0304903 A1 | 11/2013 | Mick et al. | |
| 2014/0046931 A1 | 2/2014 | Mok et al. | |
| 2014/0056243 A1 | 2/2014 | Pelletier et al. | |
| 2014/0059084 A1 | 2/2014 | Adams et al. | |
| 2014/0088981 A1 | 3/2014 | Momita | |
| 2014/0136233 A1 | 5/2014 | Atkinson et al. | |
| 2014/0222482 A1 | 8/2014 | Gautam et al. | |
| 2014/0244300 A1 | 8/2014 | Bess et al. | |
| 2014/0278491 A1 | 9/2014 | Weiss | |
| 2014/0358578 A1 | 12/2014 | Ptachcinski | |
| 2014/0358845 A1 | 12/2014 | Mundlapudi et al. | |
| 2015/0095056 A1 | 4/2015 | Ryan et al. | |
| 2015/0112696 A1 | 4/2015 | Kharraz Tavakol | |
| 2015/0142464 A1 | 5/2015 | Rusin et al. | |
| 2015/0199482 A1 | 7/2015 | Corbin et al. | |
| 2015/0332283 A1 | 11/2015 | Witchey | |
| 2016/0028552 A1 | 1/2016 | Spanos et al. | |
| 2016/0055205 A1 | 2/2016 | Jonathan et al. | |
| 2016/0253679 A1 | 9/2016 | Venkatraman et al. | |
| 2016/0328641 A1 | 11/2016 | Alsaud et al. | |
| 2016/0342750 A1 | 11/2016 | Alsaud et al. | |
| 2017/0060856 A1 | 3/2017 | Turtle | |
| 2017/0091397 A1 | 3/2017 | Shah et al. | |
| 2017/0103164 A1 | 4/2017 | Dunlevy et al. | |
| 2017/0103165 A1 | 4/2017 | Dunlevy et al. | |
| 2017/0132621 A1 | 5/2017 | Miller et al. | |
| 2017/0351821 A1 | 12/2017 | Tanner et al. | |
| 2017/0372300 A1 | 12/2017 | Dunlevy et al. | |

OTHER PUBLICATIONS

Newman, *Modularity and community structure in networks*, PNAS, vol. 103, No. 23, pp. 8581-8582 Jun. 6, 2006 (2 pgs.).

Titan Database Documentation ©2015 (disclosed at http://s3.thinkaurelius.com/docs/titan/1.0.0/ (printed Sep. 16, 2016) (214 pgs.).

Ahlswede et al., *Network Information Flow*, IEEE Transactions on Information Theory, vol. 46, No. 4; Jul. 2000 (13 pgs.).

Bhattacharya, Indrajit and Getoor, Lise, *Entity Resolution in Graphs*, Department of Computer Science, University of Maryland (2005) (21 pgs.).

Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).

Christen, *Data Matching, Concepts and Techniques for Record Linkage, Entity Resolution, and Duplicate Detection*, © Springer-Verlag Berlin Heidelberg, 2012 (279 pgs.).

Cohen et al., *A Comparison of String Metrics for Matching Names and Records*, © 2003, American Association for Artificial Intelligence (www.aaai.org) (6 pgs.).

Coleman et al., *Medical Innovation—a diffusion study*; The Bobbs-Merrill Company, Inc., 1966 (248 pgs.).

Domingos et al., *Mining High-Speed Data Streams*, (2000) (10 pgs.).

Greenhalgh et al., *Diffusion of Innovations in Health Service Organisations—a systematic literature review*, Blackwell Publishing, 2005 (325 pgs.).

(56) References Cited

OTHER PUBLICATIONS

Jackson et al., *The Evolution of Social and Economic Networks*, Journal of Economic Theory 106, pp. 265-295, 2002 (31 pgs.).
Jackson, Matthew O., *Social and Economic Networks*, Princeton University Press, 2008 (509 pgs.).
Krempl et al., *Open Challenges for Data Stream Mining Research*, SIGKDD Explorations, vol. 16, Issue 1, Jun. 2014 (64 pgs.).
Rebuge, *Business Process Analysis in Healthcare Environments*, 2011, Ellsevier Ltd., pp. 99-116 (18 pgs.).
Wasserman et al., *Social Network Analysis: Methods and Applications*, Cambridge University Press; 1994 (434 pgs.).
White et al., *Algorithms for Estimating Relative Importance in Networks*, Proceedings of the Ninth ACM SIGKDD International Conference on Knowledge Discovery and Data Mining, 2003 (10 pgs.).
(MATHJAX), *Naive Bayes Categorisation (with some help from Elasticsearch)*, blog post dated Dec. 29, 2013 (https://blog.wtf.sg/2013/12/29/naive-bayes-categorisation-with-some-help-from-elasticsearch/). (8 pgs.).
Webpage: New Health Care Electronic Transactions Standards Versions 5010, D.0, and 3.0, Jan. 2010 ICN 903192; http://www.cms.gov/Regulations-and-Guidance/HIPAA-Adminstrative-Simplification/Versions5010andD0/downloads/w5010BasicsFctCht.pdf (4 pgs.).
Webpage: U.S. Dept. of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).
Anonymous: "Oauth" Wikipedia—Retrieved from the Internet URL:https://en.wikipedia.org/wiki/Oauth (8 pgs.).
Version 5010 and D.O, Center for Medicare & Medicaid Services (2 pgs.).

\* cited by examiner

PIPELINE PROCEDURE:
1. TAKE A CLAIM REAL TIME
2. MAP IT INTO A SUB-GROUP
3. PREDICT ITS CLASSIFICATION ACCORDING TO TRAINED CLASSIFIERS:
   A. DENIED
   B. OVERPAYMENT
   C. UNDERPAYMENT
4. COLLECT 837 AND 277 PAIRINGS FOR BATCH MODEL UPDATING AND RE-TRAINING

SUBSCRIBER: Jane Smith
PATIENT ADDRESS: 236 N. Main St., Miami, FL 33413
TELEPHONE NUMBER: 305-555-1111
SEX: F
DOB: 05/01/43
EMPLOYER: ACME Inc.
GROUP #: 2222-SJ
KEY INSURANCE COMPANY ID #: JS001112223333
PATIENT: Ted Smith
PATIENT ADDRESS: 236 N. Main St., Miami, FL 33413
TELEPHONE NUMBER: 305-555-1111
SEX: M
DOB: 05/01/73
KEY INSURANCE COMPANY ID #: JS001112223333
DESTINATION PAYER: Key Insurance Company
PAYER ADDRESS: 3333 Ocean St. South Miami, FL 33000
PAYER ID: 999996666
SUBMITTER: Premier Billing Service
EDI#: TGJ23
CONTACT PERSON AND PHONE NUMBER: JERRY, 305-555-2222 ext. 231
RECEIVER: Key Insurance Company
EDI #:66783JJT

FIGURE 5A

BILLING PROVIDER: Dr. Ben Kildare,
ADDRESS: 234 Seaway St, Miami, FL, 33111
NPI: 9876543210
TIN: 587654321
KEY INSURANCE COMPANY PROVIDER ID #: KA6663
Taxonomy Code: 203BF0100Y
PAY-TO PROVIDER: Kildare Associates,
PROVIDER ADDRESS: 2345 Ocean Blvd, Miami, Fl 33111
RENDERING PROVIDER: Dr. Ben Kildare
PATIENT ACCOUNT NUMBER: 2-646-3774
CASE: Patient has sore throat.
INITIAL VISIT: DOS=10/03/06. POS=Office
SERVICES: Office visit, intermediate service, established patient, throat culture.
CHARGES: Office first visit = $40.00, Lab test for strep = $15.00
FOLLOW-UP VISIT: DOS=10/10/06 POS=Office
Antibiotics didn't work (pain continues).
SERVICES: Office visit, intermediate service, established patient, mono screening.
CHARGES: Follow-up visit = $35.00, lab test for mono = $10.00.
TOTAL CHARGES: $100.00.
ELECTRONIC ROUTE: Billing provider (sender), to VAN to Key Insurance Company (receiver). VAN claim identification number = 17312345600006351.

FIGURE 5B

Transmission Explanation
HEADER
ST*837*0021*005010X222~
ST TRANSACTION SET HEADER
BHT*0019*00*244579*20061015*1023*CH~
BHT BEGINNING OF HIERARCHICAL TRANSACTION
1000A SUBMITTER
NM1*41*2*PREMIER BILLING SERVICE*****46*TGJ23~
NM1 SUBMITTER NAME
PER*IC*JERRY*TE*3055552222*EX*231~
PER SUBMITTER EDI CONTACT INFORMATION
1000B RECEIVER
NM1*40*2*KEY INSURANCE COMPANY*****46*66783JJT~
NM1 RECEIVER NAME
2000A BILLING PROVIDER HL LOOP
HL*1**20*1~
HL - BILLING PROVIDER
PRV*BI*PXC*203BF0100Y~
PRV BILLING PROVIDER SPECIALTY INFORMATION
2010AA BILLING PROVIDER
NM1*85*2*BEN KILDARE SERVICE*****XX*9876543210~
NM1 BILLING PROVIDER NAME
N3*234 SEAWAY ST~
N3 BILLING PROVIDER ADDRESS
N4*MIAMI*FL*33111~
N4 BILLING PROVIDER LOCATION
REF*EI*587654321~
REF - BILLING PROVIDER TAX IDENTIFICATION

FIGURE 5C

2010AB PAY-TO PROVIDER
NM1*87*2~
NM1 PAY-TO PROVIDER NAME
N3*2345 OCEAN BLVD~
N3 PAY-TO PROVIDER ADDRESS
N4*MIAMI*FL*33111~
N4 PAY-TO PROVIDER CITY
2000B SUBSCRIBER HL LOOP
HL*2*1*22*1~
HL - SUBSCRIBER
SBR*P2222-SJ****CI~
SBR SUBSCRIBER INFORMATION
2010BA SUBSCRIBER
NM1*IL*1*SMITH*JANE****MI*JS001112223333~
NM1 SUBSCRIBER NAME
DMG*D8*19430501*F~
DMG SUBSCRIBER DEMOGRAPHIC INFORMATION
2010BB PAYER
NM1*PR*2*KEY INSURANCE COMPANY*****PI*999996666~
NM1 PAYER NAME
REF*G2*KA6663~
REF BILLING PROVIDER SECONDARY IDENTIFICATION
2000C PATIENT HL LOOP
HL*3*2*23*0~
HL - PATIENT
PAT*19~
PAT PATIENT INFORMATION

FIGURE 5D

2010CA PATIENT
NM1*QC*1*SMITH*TED~
NM1 PATIENT NAME
N3*236 N MAIN ST~
N3 PATIENT ADDRESS
N4*MIAMI*FL*33413~
N4 PATIENT CITY/STATE/ZIP
DMG*D8*19730501*M~
DMG PATIENT DEMOGRAPHIC INFORMATION
2300 CLAIM
CLM*26463774*100***11:B:1*Y*A*Y*|~
CLM CLAIM LEVEL INFORMATION
REF*D9*17312345600006351~
REF CLAIM IDENTIFICATION NUMBER FOR CLEARING HOUSES (Added by C.H.)
HI*BK:0340*BF:V7389~
HI HEALTH CARE DIAGNOSIS CODES
2400 SERVICE LINE
LX*1~
LX SERVICE LINE COUNTER
SV1*HC:99213*40*UN*1***1~
SV1 PROFESSIONAL SERVICE
DTP*472*D8*20061003~
DTP DATE - SERVICE DATE(S)
2400 SERVICE LINE
LX*2~
LX SERVICE LINE COUNTER
SV1*HC:87070*15*UN*1***1~
SV1 PROFESSIONAL SERVICE
DTP*472*D8*20061003~
DTP DATE - SERVICE DATE(S)

FIGURE 5E

```
2400 SERVICE LINE
LX*3~
LX SERVICE LINE COUNTER
SV1*HC:99214*35*UN*1***2~
SV1 PROFESSIONAL SERVICE
DTP*472*D8*20061010~
DTP DATE - SERVICE DATE(S)
2400 SERVICE LINE
LX*4~
LX SERVICE LINE COUNTER
SV1*HC:86663*10*UN*1***2~
SV1 PROFESSIONAL SERVICE
DTP*472*D8*20061010~
DTP DATE - SERVICE DATE(S)
TRAILER
SE*42*0021~
SE TRANSACTION SET TRAILER
```

FIGURE 5F

```
ISA*00*          *00*          *01*1234567890     *01*9999999999  *120126*1211*U*00401*000000632*0*P*\
GS*ME*1234567890  *999999999  *20120126*1211*1*T*004010
ST*277*0001
BHT*0001*00*Reference Identification***1744480
REF*01*Reference Identification*Description*01\Reference Identification\01\Reference
Identification\01\Reference Identification
HL*1**1
DMG*CC*Date Time Period*A***1
NM1*01*1*Name Last or Organization Name**Name Middle*Name Prefi***01*01
N4*City Name**POSTAL CODE*COU
PER*1A*Name*AA*Communication Number*AA*Communication Number*AA*Communication
Number*Contact Inquiry Refe
TRN*1*Reference Identification
STC*Industry Code\Industry Code\01**1*1054828173296352 4**20120314*****Industry Code\Industry Code
REF*01*Reference Identification**01\Reference Identification\\01\Reference Identification
DTP*001*CC*Date Time Period
SE*13*0001
GE*1*1
IEA*1*000000632
```

FIGURE 6

| Patient Age | CPT99203 | CPT95017 | CPT27447 | Provider_1 | Provider_2 | Provider_3 | Payer_1 | Payer_2 | Total Amount | Procedure Count |
|---|---|---|---|---|---|---|---|---|---|---|
| 42 | 32.34 | 699.99 | 0.00 | 1 | 1 | 0 | 1 | 0 | 732.33 | 2 |
| 12 | 140.82 | 0.00 | 0.00 | 0 | 0 | 1 | 0 | 1 | 140.82 | 1 |
| 67 | 25.00 | 198.95 | 0.00 | 1 | 0 | 0 | 1 | 0 | 223.95 | 2 |
| 83 | 450.00 | 0.00 | 6835.20 | 0 | 0 | 1 | 1 | 1 | 7285.2 | 2 |
| 23 | 41.23 | 0.00 | 0.00 | 1 | 0 | 0 | 0 | 1 | 41.23 | 1 |

Figure 9

DYNAMIC TOPOLOGICAL SYSTEM AND METHOD FOR EFFICIENT CLAIMS PROCESSING

PRIORITY CLAIM

This application claims priority under 35 USC 120 and is a continuation of U.S. patent application Ser. No. 14/715,380, file May 18, 2015 and entitled "Dynamic Topological System and Method for Efficient Claims Processing" the entirety of which is incorporated herein by reference.

FIELD

The disclosure relates generally to a system and method for healthcare claims processing and in particular to a dynamic topological system and method for efficient claims processing.

BACKGROUND

A healthcare marketplace system may provide a transparent health services marketplace with clear descriptions and posted prices. Many health care providers and payers use legacy systems to communicate information to the healthcare marketplace system for a variety of transactions: eligibility checks, claims processing and benefits enrollment. To integrate the healthcare marketplace system capabilities with existing systems in the health care space, it's important that it be able to process massive streams of transactional data related to health care services. The ability to process these transaction streams enables: real-time eligibility checks for quote requests, submitting a claim for a service after paying cash so that the service cost can contribute toward a deductible, and enrolling a consumer in new health benefits so that they might save money on expensive services. Integrating all of these transaction capabilities with the health service marketplace provides consumers with easy access to information to help them make informed decisions concerning their health care spending. It also provides health care providers and payers with more efficiencies so that administrative costs for processing health care transactions approach zero. Without the dynamic transactional data streaming capabilities, consumers would only be able to use the healthcare marketplace system for cash based transactions and would have to consult other systems for insurance based pricing. The dynamic transactional data streaming may provide the best possible user experience for health care consumers and providers participating in the health care services marketplace.

Since many healthcare providers and payers use legacy systems to communicate information for a variety of transactions (eligibility checks, claims processing and benefits enrollment), according to the American Medical Association ("AMA"), administrative costs associated with the processing of health care insurance claims is upwards of $210 billion per year in the United States. The AMA also estimates that as many as 1 in 5 claims is processed inaccurately leading to significant amounts of money lost due to waste, fraud, and abuse. Thus being able to accurately predict whether a claim will be denied before it is submitted to the payer as well as predicting if the claim was accurately paid after adjudication has the potential greatly improve provider's revenue cycle management.

There is a difference between a "denied" and a "rejected" claim, although the terms are commonly interchanged. A denied claim refers to a claim that has been processed and the insurer has found it to be not payable. Denied claims can usually be corrected and/or appealed for reconsideration. A rejected claim refers to a claim that has not been processed by the insurer due to a fatal error in the information provided. Common causes for a claim to be rejected include inaccurate personal information (i.e.: name and identification number do not match) or errors in information provided (i.e.: truncated procedure code, invalid diagnosis codes, etc.) A rejected claim has not been processed so it cannot be appealed. Instead, rejected claims need to be researched, corrected and resubmitted.

While there is a fair bit of literature on using data-driven methods to detect fraud and abuse in healthcare claims, there is relatively little on using these approaches for predicting denials and errors in healthcare claims. Unlike rejected claims which are erroneous due to very wrong information provided in the claim transaction, claims are denied for less obvious reasons.

Common Reasons for Denied Claims

There are many core reasons that a claim is denied. Below are a few pertinent examples of reasons for denied claims:

- Delay between claim submission and encounter: Claims will be denied to too long a time period passes between the encounter and the claim submission because payers specify the allowable amount of time between the encounter and when the claim must be submitted.
- Mismatched diagnostic and procedure codes: Claims will be denied if the diagnosis code (ICD) does not warrant the billed procedure code (CPT). Frequent itemset mining approaches such as FP-Growth and others can be used to learn positive and negative association rules between the ICD and CPT codes.
- Claim Not at billing contracted rate: If a provider accepts a payer's insurance plan, then they are held to a contracted rate for each procedure they provide for the payer's insured patients. Detecting outliers in a payer/provider/procedure tuple could be detected rather easily using linear regression, however there is one catch and that is when the contract rate changes. Thus a system must be able to deal with the concept of drift of contracted rates.
- Claim not covered: The procedures performed by the provider are not covered under the patient's insurance. Some circumstances could be caught with an eligibility check.
- Patient no longer eligible: A lot of claims are submitted where the patient is, for various reasons, no longer an insured member of the payer's plan. This could be addressed by doing an eligibility request before a claims submission.
- Preauthorization required: The procedure required preauthorization that was not performed beforehand.
- Provider is out of network: The provider is not a member of the payer's network.

The last 3 reasons (patient is not eligible, pre-auth required, and provider is out of network) are kind of moot at the point of claim submission as there is no ability to appeal since the damage is done. These should probably be moved up in the "process" at the time of the encounter to be more effective.

Previous systems have attempted to solve this problem via expert systems. These systems are cumbersome and require extensive domain knowledge.

BRIEF DESCRIPTION OF THE DRAWINGS

FIGS. 5A-5F illustrates an example of claims data in an X12 837;

FIG. 6 illustrates an example of the data in EDI 277;

FIG. 9 illustrates an example of a simplified feature matrix.

DETAILED DESCRIPTION OF ONE OR MORE EMBODIMENTS

The disclosure is particularly applicable to a claims processing system incorporated into a health system as described below and it is in this context that the disclosure will be described. It will be appreciated, however, that the system and method has greater utility since it may be implemented in other manners that those disclosed below and may be a standalone claims processing system as well as software as a service (SaaS) system that provides claims processing to a plurality of third party systems.

A healthcare marketplace system may include one or more payers of healthcare services and products, one or more healthcare service and product providers and one or more consumers of the healthcare services or products. To reduce costs for the payer, provider and consumer, a claims processing system described below provides a modeling process that will enable more efficient claims processing for medical services as described below in more detail.

Figure 1:
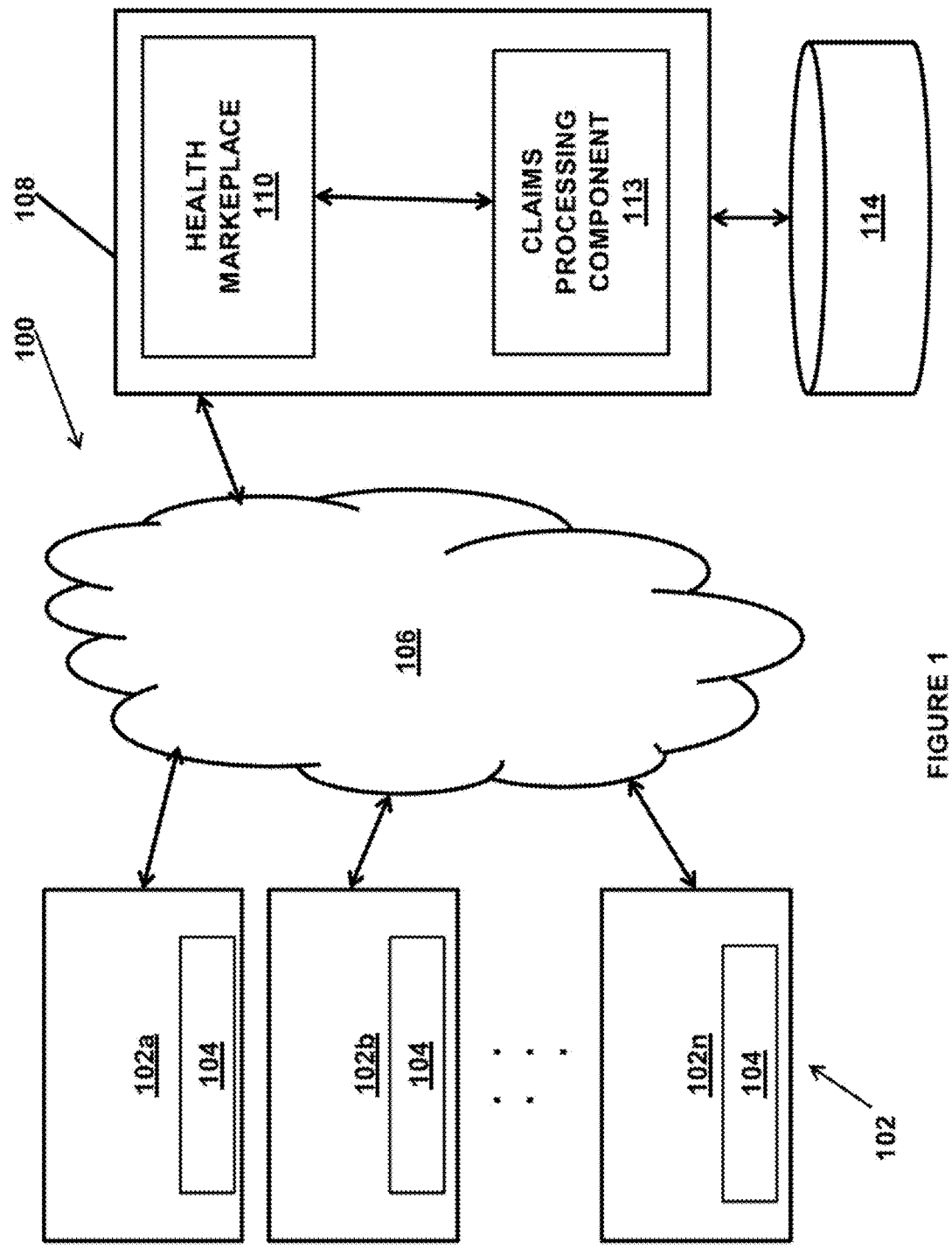
FIG. 1 illustrates a health care marketplace system that may incorporate a dynamic topological component for claims processing.

FIG. 1 illustrates an example of a health network system 100 that may incorporate a claims processing component 113. In the example in FIG. 1, the system may be implemented as a client/server, software as a service (SaaS) or a cloud based architecture. However, the system and in particular the claims processing component 113 may also be implemented on a standalone computer system that performs the operations of the claims processing component 113 as described below or the claims processing component 113 may be integrated into other systems.

In one implementation, as shown in FIG. 1, the claims processing component 113 may be integrated into a health system 100 in which one or more computing devices 102 may couple to, access and interface with a backend component 108 over a communications path 106. The backend component 108 may include a health marketplace 110 and the claims processing component 113. The health marketplace 110 may permit a user of the computing device to perform various health care related activities including shopping for health care, participating a health care blogs and forums and the like. The claims processing component 113 may, based on available data about a particular health care claim of a particular consumer, determine a claim denial score for the particular health care claim of a particular consumer. The detailed operation of the claims processing component 113 is described below in more detail.

In the system, each computing device 102, such as computing devices 102a, 102b, . . . , 102n, may be a processor based device with memory, persistent storage, wired or wireless communication circuits and a display that allows each computing device to connect to and couple over the communication path 106 to a backend component 108. For example, each computing device may be a smartphone device, such as an Apple Computer product, Android OS based product, etc., a tablet computer, a personal computer, a terminal device, a laptop computer and the like. In one embodiment shown in FIG. 5A, each computing device 102 may store an application 104 in memory and then execute that application using the processor of the computing device to interface with the backend component 108. For example, the application may be a typical browser application or may be a mobile application. The communication path 106 may be a wired or wireless communication path that uses a secure protocol or an unsecure protocol. For example, the communication path 106 may be the Internet, Ethernet, a wireless data network, a cellular digital data network, a WiFi network and the like. The system 100 may also have a storage 114 that may be connected to the backend component 108 and may store various data, information and code that is part of the system. The storage 114 may also store a claims database that contains healthcare claims related information.

The backend component 108 may be implemented using one or more computing resources, such as a processor, memory, flash memory, a hard disk drive, a blade server, an application server, a database server, a server computer, cloud computing resources and the like. The health marketplace 110 and the claims processing component 113 may each be implemented in software or hardware. When the health marketplace 110 and the claims processing component 113 are each implemented in software, each component may be a plurality of lines of computer code that reside on the backend component 108 (or are downloaded to the backend component 108) and may be executed by a processor of the backend component 108 so that the processor is configured to perform the operations of the health marketplace 110 or the claims processing component 113. When the health marketplace 110 and the claims processing component 113 and each implemented in hardware, each component may be an application specific integrated circuit, a microcontroller, a programmable logic device and the like that perform the operations of the health marketplace 110 or the claims processing component 113.

The dynamic topological system and method for efficient claims processing that may be implemented as the claims processing component 113 as described above has various advantages over known systems:

1. Easily Extensible: The system is able to allow a non-programmer person such as an Electronic Data Interchange (EDI) analysts or other subject matter experts (SME) to view, add, edit, and delete validation logic for the claims processing.
2. Maintainable: While the validations in the ASC X12 specification do not change that often, the validation requirements for 3rd party trading partners do. The validation system is designed in such a way that doesn't make it a nightmare to update validation logic. In the past this has been addressed through complex maintenance of rule engines.
3. Extendable: The system allows payer/provider/procedure specific validation logic to supercede general or global logic. Once again, the extensibility in previous embodiments has been through rule based engines where millions of rules needed to be maintained.

Classification is a well studied problem in machine learning and statistics in which the goal is to assign a new observation to a category based on a set of training data whose category assignment is known. Most classification algorithms operate by trying to optimize a function for determining classes over all of the dataset, and thus make global assumptions about the data. The claims processing system has a process for segmenting the claims datasets into local neighborhoods and then training and choosing the best classifier for each neighborhood. The methodology of making these global optimizations are germane to the process.

Figure 2:
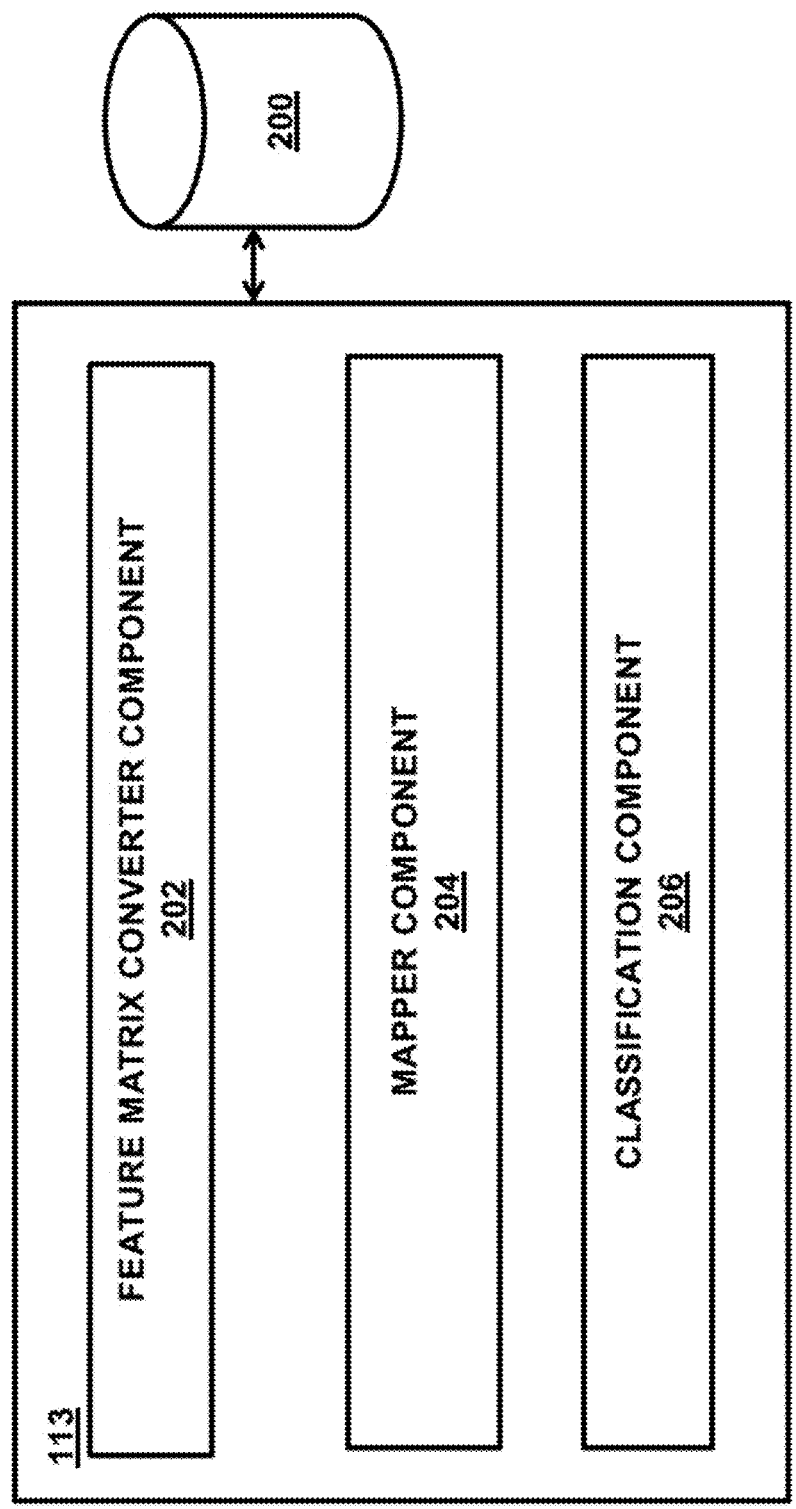
FIG. 2 illustrates more details of the claims processing component.

FIG. 2 illustrates more details of the claims processing component 113 that is associated with a claims database 200. The claims database 200 may have a plurality of pieces of data about a plurality of healthcare claims (an example of which is shown in FIGS. 5A-5F) that may be used by the system. The claims processing component 113 may have feature matrix converter component 202, a mapper component 204 and a classification component 206 that operate on the plurality of pieces of data about a plurality of healthcare claims to perform the claim processing of the system as will be described below with reference to FIGS. 3-4. Each component of the claims processing component 113 may be implemented in software or hardware. When the components are each implemented in software, each component may be a plurality of lines of computer code and may be executed by a processor of the backend component 108 (that hosts the claims processing component 113) so that the processor is configured to perform the operations of the components. When the components are each implemented in hardware, each component may be an application specific integrated circuit, a microcontroller, a programmable logic device and the like that perform the operations of the claims processing component 113 as described below in more detail.

Figure 3:
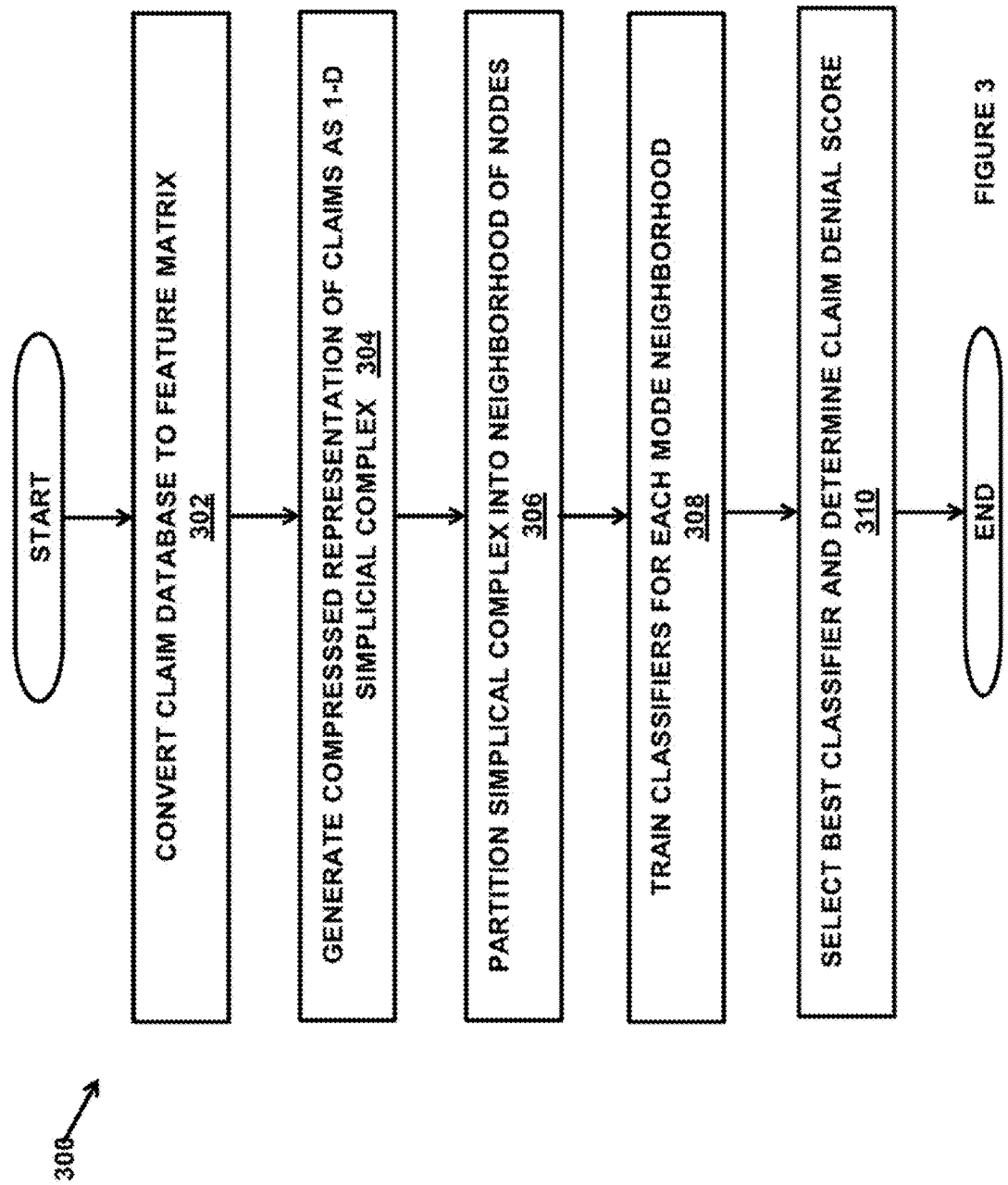
FIG. 3 illustrates a method for claims processing that may be implemented using the claims processing component.
Figure 4:
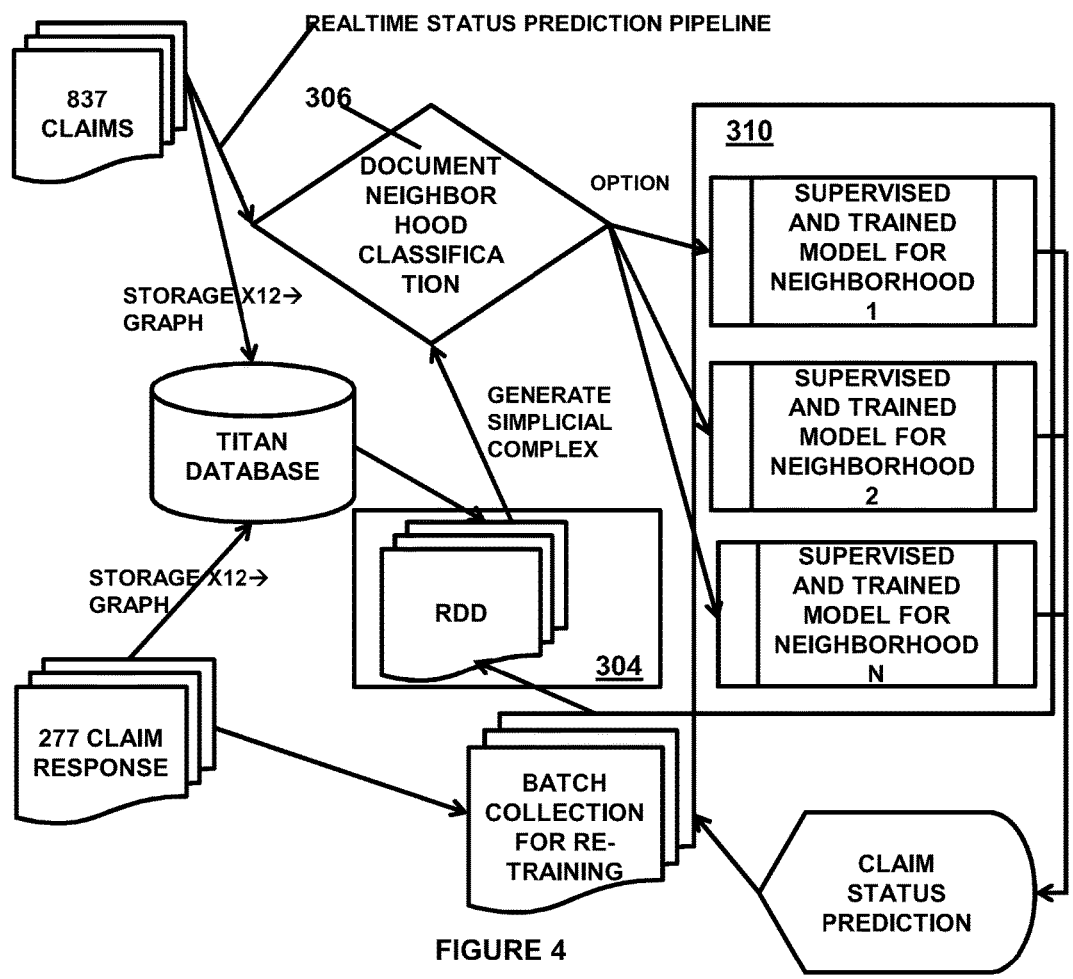
FIG. 4 illustrates a data flow of the method for claims processing.

FIG. 3 illustrates a method 300 for claims processing that may be implemented using the claims processing component and FIG. 4 illustrates a data flow of the method for claims processing. These methods may be implemented by the components in FIG. 1-2 or by other elements that are configured to perform the processes of the method.

Prior to describing the details of the method, an electronic healthcare claim data overview is provided. Health care insurance claims are transmitted electronically using the ANSI ASC X12 standard. Professional and institutional claims are submitted using the format detailed in the "ANSI ASC X12 837 Health Care Claims" specification (hereinafter referred to as "837"). The status of a health care insurance claim is described in the "ANSI ASC X12 277 Health Care Information Status Notification" transaction (hereinafter referred to as "277"). After verifying the consumer's health insurance, the provider examines the patient and makes a diagnosis. Since the provider did a general eligibility inquiry (X12 270) to determine the consumer's current deductible information, the provider is now equipped to recommend a set of treatment options that the consumer can pay for with cash or insurance. With a diagnosis and treatment(s) identified, the provider can initiate a more specific eligibility inquiry (X12 270) with codes (typically CPT or ICD-10) for the treatments to determine if the recommended treatments are covered by the consumer's insurance plan. This allows the consumer to make informed decisions regarding the treatments and their costs while they're still meeting with their health care provider. Once a treatment is selected, the health care marketplace system will record the treatment purchase transaction and submit the necessary X12 837 claims to the insurance company if the consumer elects to (partially) pay with insurance. If there is a portion of the treatment cost remaining after processing the X12 835 health care claim payment response, the health care marketplace system can then bill the consumer via their credit card on file and deposit the funds in the provider's bank account along with the insurance payment that was delivered in the X12 835 claim payment transaction set.

An example of the data in the X12 837 health care claims record is in FIGS. 5A-5F. In the record, a patient is a different person than the Subscriber and the payer is commercial health insurance company.

An example of the data in the X12 277 record is shown in FIG. 6. The EDI 277 Health Care Claim Status Response transaction set is used by healthcare payers (insurance companies, Medicare, etc.) to report on the status of claims (837 transactions) previously submitted by providers. The 277 transaction, which has been specified by HIPAA for the submission of claim status information, can be used in one of the following three ways:

A 277 transaction may be sent in response to a previously received EDI 276 Claim Status Inquiry (described in more detail at https://www.ledisource.com/transaction-sets?tset=276 which is incorporated by reference)

A payer may use a 277 to request additional information about a submitted claim (without a 276)

A payer may provide claim status information to a provider using the 277, without receiving a 276

Information provided in a 277 transaction generally indicates where the claim is in process, either as Pending or Finalized. If finalized, the transaction indicates the disposition of the claim—rejected, denied, approved for payment or paid. If the claim was approved or paid, payment information may also be provided in the 277, such as method, date, amount, etc. If the claim has been denied or rejected, the transaction may include an explanation, such as if the patient is not eligible.

The 276 transaction can be received from the trading partner at the line level. The 276 request is a solicited request that is made by the Trading Partner. The 277-response transaction will only be returned when a solicited 276 is received. The following STC data elements will be returned on the 277 transaction depending if the claim was paid or rejected:

STC 05—Claim Payment Amount: This element will be used to reflect the claim paid amount. When a claim is not paid or the adjudication period is not complete this amount will be 0 (zero).

STC 06—Adjudication or Payment Date: This element will be used to reflect the date the claim was paid or rejected. If the claim in being inquired about has not completed the adjudication cycle, this field will not be populated.

STC 07—Payment Method Code: This element will be used to reflect the type of method that will be used to pay the adjudicated claim. This element will not be used for claims that are in process, have not completed the adjudication process, or have rejected.

STC 08—Check Issue or EFT Date: This element will be used to reflect the date that the check was produced or the date the EFT funds were released. This element will only be used for claims that have completed and adjudication and payment cycles.

STC 09—Check Number: This element is required by HIPAA for all paid and finalized claims, when the entire claim has been paid using a single check or EFT. This element will not be used for claims that are in process, have not completed the adjudication process, or have rejected.

Returning to FIGS. 3 and 4, during the method, claims data (that may be in a claims database for example) may be converted into a feature matrix (302) and then stored, such as in a Titan database as shown in FIG. 4. The 837 and 277 messages (examples of which were provided above) may be received in plain text and must be transformed into a feature matrix, F. The columns of the matrix represent numeric features of the claim and each row is a single claim instance, thus the dimensions of the F will be n×m where n is the number of claims in the database and m is the number of features. The column space of this feature matrix has the potential to be very large due to the need to categorize CPT codes, provider NPIs, and trading partner IDs, i.e. there would be a column for each of the approximately 9800 CPT codes, 4.5 million providers, and 1000 trading partners. Other features of the claim would be present as well, including but not limited to, the time between patient encounter and claims submission, total number of procedures itemized in the claim, total amount billed, etc. A very simple example of a feature matrix is shown in more detail in FIG. 9. As shown in FIG. 9, the feature matrix may have one or more columns that contain information about each claim, such as a patient age, one or more billed procedure codes (CPTs), provider information, total amount of the claim and a procedure count. Each row of the feature matrix contains the information for a particular claim made by a particular patient.

Generate a Compressed Representation

Since there are a multitude of singular and interrelated reasons a claim can be denied, it can be difficult to train a single classifier that can accurately account for all the cases. The mapper component may compress the claims database into a combinatorial structure. This process allows us to identify claims that are similar in some sense and then build specific classifiers for these similar groups, thus making a more accurate and robust classification system that provides more intuitive reasons for the classification assignments.

Figure 7:
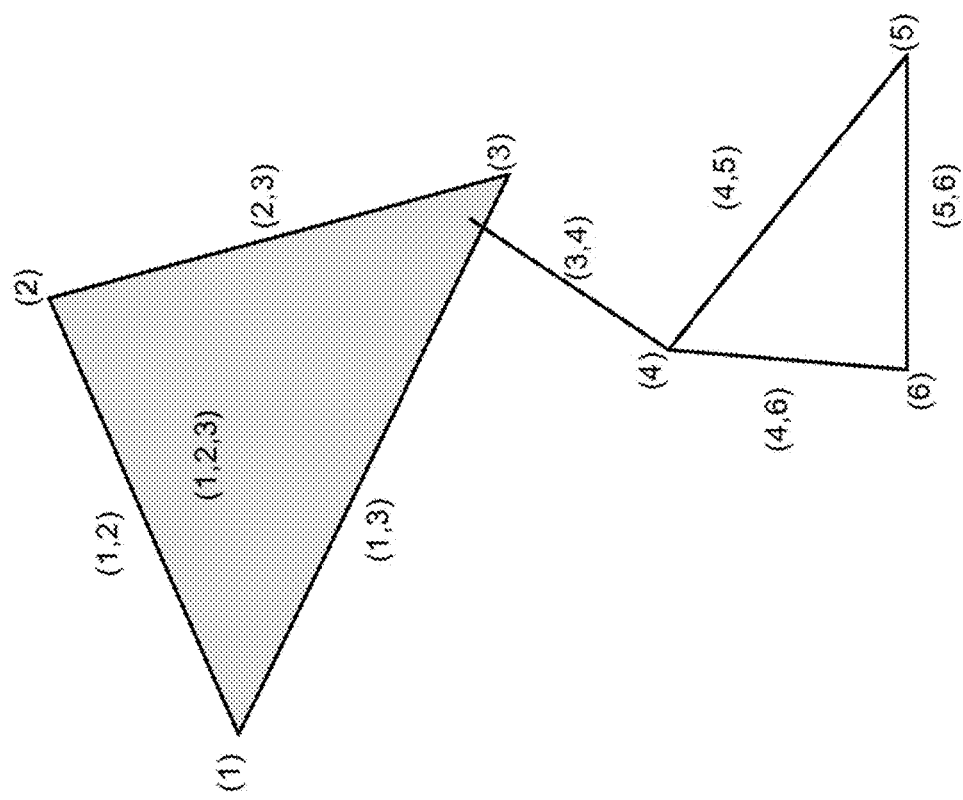
FIG. 7 illustrates an example of a simplicial complex.

Thus, once the feature matrix is generated, the method may use the feature matrix and generate a compressed representation of the claims database (304) using the mapper component. In one embodiment, the compressed representation also may be generated based on a user supplied filter function. In one embodiment, the compressed representation may be a 1-dimensional simplicial complex (304), an example of the simplicial complex is shown in FIG. 7.

The process 304 takes a feature matrix F and produce a simplicial complex which is a compressed representation of F, yet still possesses certain topological properties of the original space.

Definition:

A simplex is a generalization of a triangle or tetrahedron to arbitrary dimensions. More formally a k-simplex is the convex hull of k+1 vertices. Thus a 0-simplex is a point, a 1-simplex is a line segment, a 2-simplex is a triangle, a 3-simplex is a tetrahedron, etc.

Definition:

A simplicial complex is topological space created by "gluing" simplices such that the gluing is done along faces of the simplices. More formally, a simplicial complex K is a set of simplices such that:

1. Any face of a simplex in K is in K
2. The intersection of any two simplices $\sigma_1$, $\sigma_2 \in K$ is both of a face of $\sigma_1$ and $\sigma_2$ The process to generate the simplicial complex output may include:

1. Use a specified filter function, $f$, to map the claims feature matrix F to a parameter space P.
2. Choose a scheme that defines an open cover U on the parameter space
3. Choose a clustering algorithm and for each set in the open cover, cluster in the preimage of $f$ for that set; and
4. Represent each cluster as a node in the simplicial complex output and join any 2 nodes by an edge if a claim is a member of both clusters.

Choose a Filter Function

Filter functions are functions such that $f: F \to P$ where F is the claims feature matrix and P, the parameter space, is a topological space, such as $\Re$, $\Re^2$, or $S^1$. Often these filter functions are functions that demonstrate some geometric or connectivity properties of the data set F, such as a centrality measure from geometry or a kernel density estimator from statistics. Filter functions can also be defined by domain experts to reflect important properties of the data, i.e. the amount of time that has passed between a patient encounter and when the claim was submitted.

Filter Function Examples

Below are explanations of popular filter functions in the literature that work on any data set that has a notion of distance or similarity between points.

Gaussian Kernel Density Estimator

Kernel density estimation is a well developed area of statistics and is a nonparametric method to estimate the probability density function of a given random variable.

Gaussian Kernel Density Estimator Algorithm

---
Let $\in$ = the smoothness parameter
Let n = the number of rows of F
Let m = the number of columns of F
For each point x $\in$ F:
  Let density$_x$ = 0
  For each point y $\in$ F such that y ≠ x:
    d = dist(x, y)

$$estimate_{point} = \frac{e^{-\frac{d^2}{2\epsilon^2}}}{n(\sqrt{2\pi e})^m}$$

density$_x$ = density$_x$ + estimate$_{point}$

---

Eccentricity

Eccentricity measures are functions that identify which points in the data set are far away from the "center" where an intrinsic notion of centrality is derived from the pairwise distances of the points in the space.

Eccentricity Algorithm

---
Let exponent = be the eccentricity exponent
Let n = the number of rows of F
For each point x $\in$ F:
  if exponent == $\infty$:
    $d_{max}$ = 0
    For each point y $\in$ F:
      d = dist(x, y)
      if d > $d_{max}$:
        $d_{max}$ = d
    eccentricity$_x$ = $d_{max}$
  else:
    eccentricity$_x$ = 0
    For each point y $\in$ F:
      d = dist(x, y)$^{exponent}$
      eccentricity$_x$ = eccentricity$_x$ + d $$eccentricity_x = \frac{1}{n}(eccentricity_x)^{1/exponent}$$

---

Define a Cover Over the Image of $f$

Once a filter function is chosen, the method may choose a scheme for defining a cover over the image space of the filter function $f$.

Definition:

An open cover of a topological space X is a collection of open sets whose union contains X as a subset. More formally, if $C = \{U_\alpha : \alpha \in A\}$ is a family of open sets $U_\alpha$ and A is a finite indexing set, then C is a cover of X if $X \subseteq \cap_{\alpha \in A} U_\alpha$ There are 2 parameters in defining the cover; the number of open sets (n) and the percent overlap (p) between them.

Example Cover Schemes

Uniform Cover

Here the n open sets in the cover of the parameter space are sized so that each open set covers the same amount of the parameter space, i.e.

$$|U_\alpha|=|U_\beta| \forall U \in C$$

Uniform Cover Example

Input

Let filter_values=[1,2,3,4,5,6]

Let n=3

Let p=0.5

Output

[{'open_set_idx': 0, 'max': 3.5, 'min': 1.0},
{'open_set_idx': 1, 'max': 4.75, 'min': 2.25},
{'open_set_idx': 2, 'max': 6.0, 'min': 3.5}]

Balanced Cover

Here the n open sets in the cover of the parameter space are sized so that each open set covers the same amount of the original data space, i.e.

$$|f^{-1}(U_\alpha)|=|f^{-1}(U_\beta)| \forall U \in C$$

Balanced Cover Example

Input

Let filter_values=[1,1,2,2,5,6]

Let n=3

Let p=0.5

Output

[{'open_set_idx': 0, 'max': 1.45150502, 'min': 1},
{'open_set_idx': 1, 'max': 3.67725753, 'min': 1.44091416},
{'open_set_idx': 2, 'max': 6, 'min': 3.64548495}]

Clustering in the Preimage of $f$

Now, the method has generated an open cover of the parameter space that is a collection of overlapping open sets denoted C. Next, the method may use an arbitrary clustering algorithm, clust, as a statistical replacement for determining the number of connected components in the inverse image of $f$ for each open set in the cover. More precisely, $$\text{Clusters}=\text{clust}(f^{-1}(U_\alpha)) \forall U_\alpha \in C.$$

Examples of Possible Clustering Algorithms

Hierarchical Clustering with one of the following linkage functions:
  Single
  Complete
  Average
  Weighted
  Centroid
  Median
  Ward
K-means Clustering
K-medians Clustering
DBSCAN
Self-organizing Map Define Mapper Output Finally, the method defines an abstract simplicial complex using the clusters created above. For each cluster c in Clusters we add a 0-dimensional simplex, or vertex, to the complex. Next $\forall c_i, c_j \in$ Clusters such that $i \neq j$ we add a 1-dimensional simplex, or edge, between $c_i$ and $c_j$ if $c_i \cap c_j$ is non-empty.

Example Simplicial Complex Output (an Example of which is Shown in FIG. 7)

{'0-dimensional simplicies': [(1), (2), (3), (4), (5), (6)],
'1-dimensional simplicies': [(1,2), (1,3), (2,3), (3,4), (4,5), (4,6), (5,6)],
'2-dimensional simplicies': [(1,2,3)]}

Group Nodes in the Simplicial Complex Output into Neighborhoods

Figure 8:
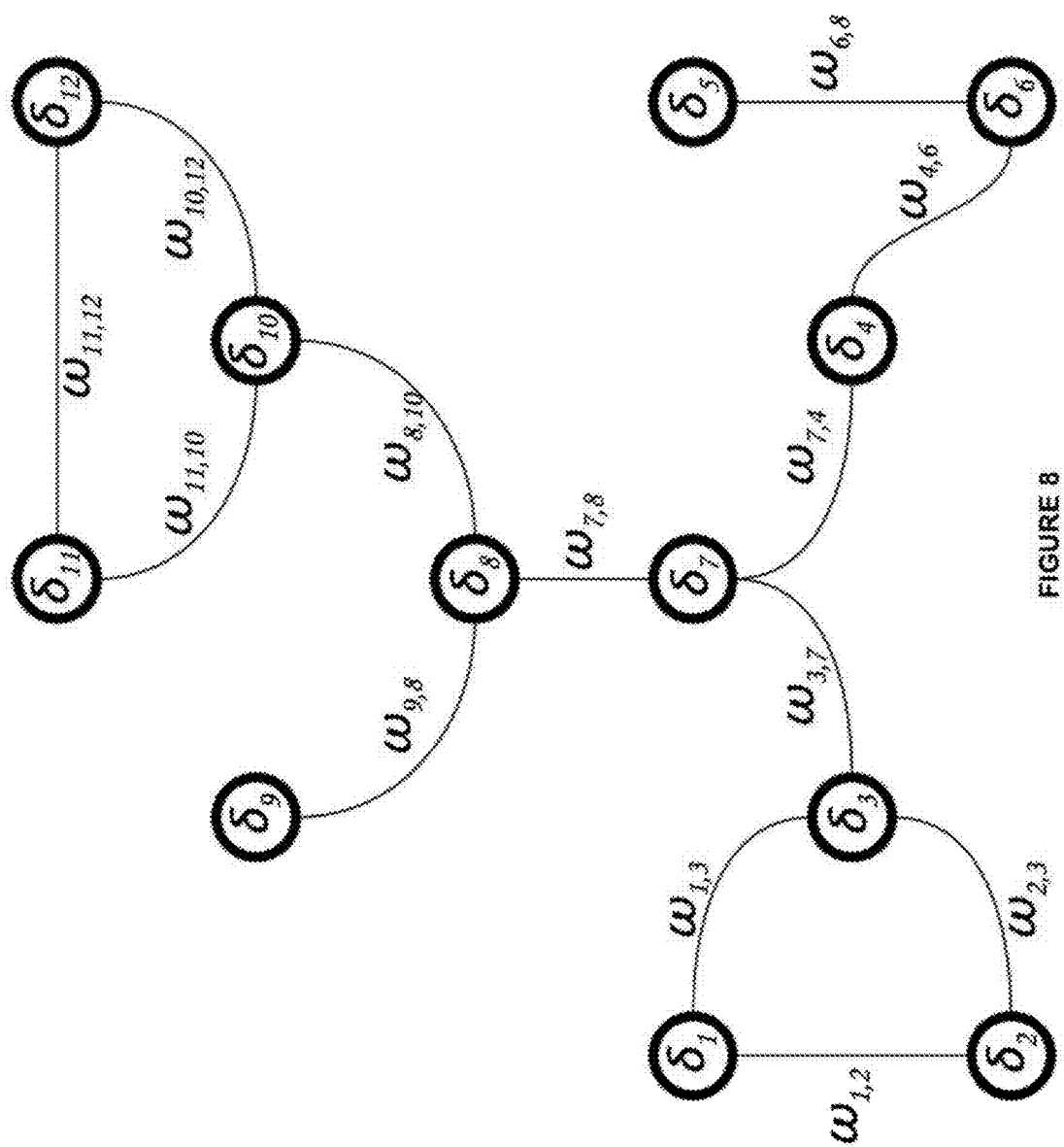
FIG. 8 illustrates an example of a weighted graph.

Returning to the method in FIGS. 3-4, the method may then partition the simplicial complex into neighborhoods of nodes (306). In one embodiment, the method may represent the 1-dimensional simplicial complex as a weighted, undirected graph G=(V,E) where each vertex $v_i \in V$ represents a group of claims $c_i$ and each edge $e_{i,j} \in E$ joins two vertices $v_i$ and $v_j$ if and only if $c_i \cap c_j \neq \emptyset$. Each vertex $v_i \in V$ has a weight $\delta_i$ and each edge $e_{i,j} \in E$ has a weight $\omega_{i,j}$. An example of a weighted graph described above in shown in FIG. 8.

The method applies techniques in community detection to detect a natural division of vertices into non-overlapping groups or communities where these communities may be of any size. This the method seeks to determine a partition K of the vertices V such that $$K=\cap_i k_i=V.$$

Techniques in community detection are sensitive to both the neighborhood structure and weights of the graph's adjacency matrix. As such, the method seeks to combine domain knowledge with graph invariants to calculate an optimal division. For example, the method may use a weighting scheme in the graph from the distribution of documents in the clusters of the preimage of $f$, as described in the previous section. That is to say, each vertex's weight would be $\delta_i=|c_i|$, which is the number of claims belonging to the cluster in the preimage of $f$; further, each edge's weight could be $\omega_{i,j}=c_i \cap c_j$, which is the count of documents in the intersection of each cluster in the preimage of $f$.

When paired with graph invariants such as, but not limited to, vertex degree, domination sets, clique assignment, connectedness, topological index, strength, capacity, independence . . . etc, the combination of domain knowledge with techniques in graph analysis yields a myriad of variations to the weighted adjacency matrix of the simplicial complex. The method seeks to utilize the combination of domain knowledge from both graph theory and this application space to determine the optimal division of a weighted or unweighted graph into communities for the overall analytics pipeline.

Graph theoretic techniques in discovering groups of vertices within a graph have a long standing history and can be generally divided into two groups. One set of methodologies, commonly referred to as graph partitions, seek to divide the vertices of a network for applications in parallel computing. A second set of approaches, known as community detection algorithms or hierarchical clustering, utilize adjacency structures to identify community structure within a graph. The methodology described herein best fits with the second class of algorithms and seeks to label natural divisions within the simplicial complex graph G in an unsupervised manner.

Algorithms in community detection attempt to divide the graph of interest into natural subgroups; typically the number and size of the groups are determined by the network itself. Further, first approaches in community detection assume that it not such division may exist. The addition of each community's modularity score introduces a level of optimization to the problem; the application seeks to find the natural subdivision that optimizes the graph's modularity score. As with typical approaches in community detection, this methodology in graph division, which optimizes the graph's modularity score, is not bounded by the number or size of each sub graph.

The method may approach the optimization problem in stages with heavy emphasis on the significance of the distribution of vertex and edge weight. That is to say, community detection in a graph identifies sub communities by selecting a minimum cut in the graph that establishes two separate, but adjacent, sub communities. The minimum cut of a graph is an edge or set of edges which, when removed, separates the graph into two disjoint components in such a way that minimizes the quantifiable difference between the components of the resulting division using an invariant of interest.

In the method, the weighted variation of a simplicial complex can represent the distribution of the document set population throughout the vertices and edges in the graph. When applying methodologies for sub community detection in a weighted graph, the relationship of an edge's weight carries two elements of significance for classifying the edge as a separation or shared adjacency between two sub-communities. First, the edge weight's position in the distribution of all edge weights in the graph yields one measure of connectivity significance as it relates to all adjacencies across the network. Secondly, in the method, the edge and vertex weights can be directly related to the population sizes for each respective community. As such, the strength associated with each adjacency is also locally related to the total weight of each vertex on the edge.

In the most basic application, the identification of a minimum cut in a graph identifies the edge, or set smallest set of edges, which would split the graph into two disjoint components upon their removal. In a weighted graph, the identification of a minimum cut identifies the smallest valued edge, or smallest accumulated value within a set of edges, which would split the graph into two disjoint components upon their removal. When optimizing over the number of edges and resulting components, trivial solutions identify the partitioning of leaves as optimal solutions or suggest no division at all. As a result, community detection algorithms seek to optimize other graph invariants which preserve community structure after the division.

Thus, the method applies methodologies in community detection which optimize the modularity score of the unweighted or weighted simplicial complex. One such methodology divides a graph according to its modularity score. A modularity score is a quantification of true community structure within the subgraph, as relates to all potential adjacencies across the graph. More formally, a graph's modularity score is the number of edges within a group minus the expected number of edges in an isomorphic graph with random edge assignment. (derived formulation below) The modularity score was designed to measure the strength of division of a network into separate clusters or communities. A modularity score for a graph can range; a graph with a high modularity has dense connectivity between identified sub-graphs but sparse connections between nodes in different sub-graphs. The literature on community detection algorithms suggest that optimizing the maximum modularity score for a graph division is the way to both divide a network into subnetworks while preserving the inherent community structure. existing work applies simulated annealing, greedy algorithms, and extremal optimization to identify the best network division via measuring the graph's modularity score.

Optimal Division of a Network into Two Communities

The method may represent the 1-dimensional simplicial complex as a weighted and undirected graph G=(V,E) where |V|=n and |E|=m. We denote $A_{ij}$ to be the weighted or binary adjacency matrix of G. The method seeks to discover the natural division of the graph G into non-overlapping communities that can be of any size and then can apply the methodology of optimal modularity to divide and discover such a partition. In addition, the use of other techniques in graph division such as, but not limited to, clique analysis, dominating sets, independent sets, connectivity, small-world property, heavy-tailed degree distributions, clustering, statistical inference, partitionings, . . . etc, may be used.

When applying the modularity score, the method initializes the problem by dividing the graph G into two groups and assigning a parameter $s_i$ to every vertex $v_i \in V$ where $s_i=1$ if $v_i$ is in group 1 and $s_i=-1$ if $v_i$ is in group 2. Generally speaking, the modularity score of this graph partition is understood to be the density of the edges within each community minus the expected number of edges between the groups.

The expected number of edges between any two vertices, denoted herein with $E_{ij}$, preserves the degree distribution of the graph while considering all possible graphs with the same distribution. For any two vertices $v_i$ and $v_j$ we calculate $E_{ij}$ as follows:

$$E_{ij} = \frac{\delta(v_i) \cdot \delta(v_j)}{2m}$$

where $\delta(v_i)$ denotes the degree of vertex $v_i$ and $|E|=m=\frac{1}{2} \cdot \Sigma_{v \in V} \delta(v_i)$. Thus, the modularity is $A_{ij}-E_{ij}$ for all pairs of vertices in the same group, and zero otherwise. Following the work in Neumann, we represent the modularity matrix as follows:

$$Q = \frac{1}{4m} s^T B s$$

where s is the column vector of graph partition assignments and the matrix $B=A_{ij}-E_{ij}$. By writing s as a linear combination of the normalized eigenvectors $u_i$ of B where $s=\Sigma_{i=1}^n \alpha_i u_i$ where $\alpha_i=u_i^T \cdot s$, then we have:

$$Q = \frac{1}{4m} s^T B s = \frac{1}{4m} \sum_{i=1}^n \alpha_i u_i^T B \sum_{i=1}^n \alpha_i u_i = \frac{1}{4m} \sum_{i=1}^n (u_i^T \cdot s)^s \cdot \beta_i$$

where $\beta_i$ is the eigenvalue of B corresponding to eigenvector $u_i$. With the assumption that the eigenvalues are labeled in decreasing order $\beta_1 \geq \beta_2 \geq \ldots \geq \beta_n$, the method may maximize the modularity by choosing an appropriate division of the network by choice of the index vector s.

Optimal Division of a Network into n Communities

As detailed in Newman, Mark E J. "Modularity and community structure in networks." *Proceedings of the National Academy of Sciences* 103.23 (2006): 8577-8582, this procedure works for applications when the sizes of the communities are not specified. In this process, there is a trivial solution vector s=<1, 1, . . . 1>, but the corresponding eigenvalue is zero. Further, it is also important to note that eigenvalues of the modularity matrix may all be negative. In this case, this method implies that no further division of the network will improve the modularity score and therefore the solution is that no further division exists. This then gives the algorithm for dividing the network: the method computes the leading eigenvector of the weighted adjacency matrix and divides the vertices into two groups according to the signs of the elements in this vector. The method stops when the leading eigenvalue is nonpositive. The weighted adjacency matrix can be constructed as a modularity matrix, or some other combination of graph invariants with application knowledge.

The above process describes the procedure for discovering the optimal partition of a graph into two sets and the method may iteratively apply this technique in a greedy manner to discover the natural division of the graph G into non-overlapping communities that can be of any size. As such, the process for optimizing the resulting number and size of communities will be as follows:

```
optimal_split(G):
    initialize s_i with a random partition
    calculate matrices:
```

$$E_{ij} = \frac{\delta(v_i) \cdot \delta(v_j)}{2m}$$

```
    B = A_ij - E_ij
    calculate eigenvectors and eigenvalues β_1 of B
    sort eigenvalues such that β_1 ≥ β_2 ≥ ... ≥ β_n
    if β_1 ≤ 0:
        s_i = 1 ∀ i
    else:
        for element μ_i in normalized eigenvector u_1 of β_1:
            if μ_i ≤ 0:
                s_i = 1
            else:
                s_i = -1
```

$$Q = \frac{1}{4m} s^T B s$$

```
    if Q > 0:
        optimal_split(v ∈ V(G) where s_i = 1)
        optimal_split(v ∈ V(G) where s_i = -1)
```

The above pseudo code for optimal_split(G) describes the process of network division according to principal eigenvalue calculation and binary neighborhood assignment from the associated eigenvector. Other techniques in graph divisions such as, but not limited to, clique analysis, dominating sets, independent sets, connectivity, small-world property, heavy-tailed degree distributions, clustering, statistical inference, partitionings, . . . etc, may be used and yield a desired graph partition for this analytics architecture.

Train Group of Classifiers on Each Node Neighborhood

Returning to FIGS. 3-4, the method may, for each node neighborhood, train a set of classifiers on all the claims vectors in the feature matrix associated to that neighborhood (308) and then select a best classifier (310) to determine the status (denial, overpayment or underpayment) of a particular claim. In the processes described above, the method has compressed the original claims database into an abstract graph where each node in the graph represents a group of claims in the original database and there is an edge between two nodes if the claim groups overlap in anyway and the method used graph invariants and techniques in node partitioning to group the nodes into neighborhoods. The method may use a "bucket of models" approach to train a classifier for each node neighborhood. We define bucket={$C_0$, $C_1$, . . . , $C_n$} where each $C_i$ is a classifier and neighborhoods={$N_0$, $N_1$, . . . , $N_m$} is the collection of node neighborhoods of the simplicial complex.

For example let Ni be an arbitrary node neighborhood and let bucket={SVM, RandomForest, LogisticRegression}. The method randomly splits the data points in Ni into a training set and cross validation set, where 80% of the data points are used for training and the remaining 20% are held out for cross validation. For each classification algorithm in the bucket (SVM, RandomForest, LogisticRegression in this example), the method trains the algorithm on the training set and then uses the cross validation data set to calculate the root mean squared error of the classifier. The method then chooses the classifier for Ni that has the lowest root mean squared error.

In one embodiment, a method for selecting the best classifier for each neighborhood may be:

For each $N_i$∈neighborhoods:
    Let data=all claim vectors associated with all nodes in $N_i$
    For each $C_i$∈bucket:
        Do c times: (Where c is some constant)
        Randomly divide data into two datasets: A, and B.
        Train $C_i$ with the A
        Test $C_i$ with B
Select the classifier or combination thereof that obtains the highest average score.

For example, using the claim example in FIG. 5A-5F, the claims database was used to produce the mapper output simplicial complex as described above and then this simplical complex was partitioned into node neighborhoods using the process described above. The method then coverts the claim into a vector using the same process that converted the claim database into the feature matrix and employ the filter function used in the mapper process to determine which node neighborhood the claim vector belongs to in which that neighborhood may be designated Neighborhoodi. The method then looks up the best trained classifier for Neighborhoodi, which lets assume is RandomForesti in this example. Since RandomForesti is a trained classifier for Neighborhoodi, we can use it to predict the class of the claim vector. The possible classes the classifier could predict would be "Denied" or "Accepted".

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A healthcare claims processing apparatus, comprising:
a computer system having a processor and a memory;
a database associated with the computer system that stores one or more claims records wherein each claim record contains data about a claim and the database stores data about a plurality of claims;
a claims processing component that generates a compressed representation of the plurality of claims including a particular claim in the one or more claims records, the compressed representation having a plurality of nodes with which the particular claim is associated, partitions the compressed representation into one or more neighborhoods of nodes using a weighted undirected graph having a plurality of vertexes and a plurality of edges that connect two of the plurality of vertexes and each vertex represents a neighborhood of nodes and has a weight and each edge joins two vertexes only if at least one of the claims in the two vertexes exists in each vertex, identifies the neighborhood of nodes that includes the particular claim and determines, using a classifier for the identified neighborhood of nodes for the particular claim, a status of the particular claim, wherein the status is one of denied, overpaid or underpaid.

2. The apparatus of claim 1, wherein the compressed representation is a simplicial complex.

3. The apparatus of claim 2, wherein the claims processing component converts the one or more claims records into a feature matrix before generating the compressed representation of the one or more claims records.

4. The apparatus of claim 1, wherein the claims processing component trains one or more classifiers for each neighborhood of nodes.

5. The apparatus of claim 4, wherein the claims processing component selects a best classifier from the trained classifiers for a particular neighborhood of nodes wherein the particular claim is associated with the particular neighborhood of nodes.

6. The apparatus of claim 1, wherein the claims processing component gathers the status of the claim and feeds back the status of the claim.

7. A method for healthcare claims processing, comprising:
obtaining one or more claims records wherein each claim record contains data about a claim;
generating a compressed representation of a plurality of claims including a particular claim in the one or more claims records, the compressed representation having a plurality of nodes with which the particular claim is associated;
partitioning the compressed representation into one or more neighborhoods of nodes using a weighted undirected graph having a plurality of vertexes and a plurality of edges that connect two of the plurality of vertexes and each vertex represents a neighborhood of nodes from the plurality of claims and each edge joins two vertexes only if at least one of the claims in the two vertexes exists in each vertex;
identifying the neighborhood of nodes that includes the particular claim; and
determining, using a classifier for the identified neighborhood of nodes for the particular claim, a status of the particular claim, wherein the status is one of denied, overpaid or underpaid.

8. The method of claim 7, wherein the compressed representation is a simplicial complex.

9. The method of claim 8 further comprising converting the one or more claims records into a feature matrix before generating the compressed representation of the one or more claims records.

10. The method of claim 7, wherein determining using the classifier further comprises training one or more classifiers for each neighborhood of nodes.

11. The method of claim 10, wherein determining using the classifier further comprises selecting a best classifier from the trained classifiers for a particular neighborhood of nodes wherein the particular claim is associated with the particular neighborhood of nodes.

12. The method of claim 7 further comprising gathering the status of the claim and feeding back the status of the claim.

13. A healthcare system, comprising:
a computer system having a processor and a memory;
a health marketplace system hosted by the computer system;
a database associated with the computer system that stores one or more claims records wherein each claim record contains data about a claim and the database stores data about a plurality of claims;
a claims processing component that generates a compressed representation of the plurality of claims including a particular claim in the one or more claims records, the compressed representation having a plurality of nodes with which the particular claim is associated, partitions the compressed representation into one or more neighborhoods of nodes using a weighted undirected graph having a plurality of vertexes and a plurality of edges that connect two of the plurality of vertexes and each vertex represents a neighborhood of nodes from the plurality of claims and each edge joins two vertexes only if at least one of the claims in the two vertexes exists in each vertex, identifies the neighborhood of nodes that includes the particular claim, and determines, using a classifier for the identified neighborhood of nodes for the particular claim, a status of the particular claim, wherein the status is one of denied, overpaid or underpaid.

14. The system of claim 13, wherein the compressed representation is a simplicial complex.

15. The system of claim 14, wherein the claims processing component converts the one or more claims records into a feature matrix before generating the compressed representation of the one or more claims records.

16. The system of claim 13, wherein the claims processing component trains one or more classifiers for each neighborhood of nodes.

17. The system of claim 16, wherein the claims processing component selects a best classifier from the trained classifiers for a particular neighborhood of nodes wherein the particular claim is associated with the particular neighborhood of nodes.

18. The system of claim 13, wherein the claims processing component gathers the status of the claim and feeds back the status of the claim.

* * * * *